US007820752B2

(12) United States Patent
Bavouzet et al.

(10) Patent No.: US 7,820,752 B2
(45) Date of Patent: Oct. 26, 2010

(54) USE OF CHARGED AMPHIPHILIC STATISTIC POLYMERS FOR THICKENING PHASE COMPRISING GIANT MICELLES OF SURFACTANTS AND AQUEOUS COMPOSITION COMPRISING SAME

(75) Inventors: Bruno Bavouzet, Gentilly (FR); Pascal Chapon, Toulouse (FR); Dominic Wai-Kwing Yeung, Mississagua (CA)

(73) Assignee: Rhodia Chimie, Cedex (FR)

( * ) Notice: Subject to any disclaimer, the term of this patent is extended or adjusted under 35 U.S.C. 154(b) by 281 days.

(21) Appl. No.: 10/499,456

(22) PCT Filed: Dec. 20, 2002

(86) PCT No.: PCT/FR02/04498

§ 371 (c)(1),
(2), (4) Date: Feb. 7, 2005

(87) PCT Pub. No.: WO03/054350

PCT Pub. Date: Jul. 3, 2003

(65) Prior Publication Data

US 2005/0119401 A1    Jun. 2, 2005

(30) Foreign Application Priority Data

Dec. 21, 2001    (FR) .................................. 01 16712

(51) Int. Cl.
*C08L 31/00* (2006.01)
*C08F 20/06* (2006.01)
*C08F 118/02* (2006.01)

(52) U.S. Cl. ..................... 524/556; 526/317.1; 526/319

(58) Field of Classification Search ................ 524/556; 526/317.1, 319
See application file for complete search history.

(56) References Cited

U.S. PATENT DOCUMENTS 5,964,295 A * 10/1999 Brown et al. ............. 166/308.2

OTHER PUBLICATIONS

Encyclopedia of Surface and Colloid Science; vol. ,4; edited by Arthur T. Hubbard; © 2002 by Marcel Dekker, Inc.; four pages.
Gums and Stabilisers For The Food Industry; Special Publication No. 251; ISBN 0-85404-820-0; © The Royal Society of Chemistry 2000, four pages.
Handbook of Detergents; Surfactant Science Series vol. 82; Part A; properties; edited by Guy Broze; ISBM: 0-8247-14172; © 1999 by Marcel Dekker, Inc.; three pages.
The Merck Index: An Encyclopedia of Chemicals, Drugs, and Biologicals; Eleventh Edition; published by Merck & Co., Inc.; Rahway, N.J., U.S.A. 1989; two pages.

* cited by examiner

*Primary Examiner*—William K Cheung
(74) *Attorney, Agent, or Firm*—Hunton & Williams LLP

(57) ABSTRACT

The invention concerns the use as thickening agent of an aqueous composition comprising at least 5 wt. % of one or several phase-organized surfactant(s) comprising giant micelles whereof the average length represents at least four times the mean diameter, of at least a charged statistic amphiphilic polymer soluble in the aqueous composition, said amphiphilic polymer being used in a content such that the viscosity of the aqueous composition comprising the amphiphilic polymer is at least three times higher than that of the composition without amphiphilic polymer and than that of an aqueous composition comprising only the amphiphilic polymer. The invention also concerns aqueous compositions comprising said amphiphilic polymer, and are particularly designed for cosmetic uses.

25 Claims, No Drawings

USE OF CHARGED AMPHIPHILIC STATISTIC POLYMERS FOR THICKENING PHASE COMPRISING GIANT MICELLES OF SURFACTANTS AND AQUEOUS COMPOSITION COMPRISING SAME

This application is an application under 35 U.S.C. Section 371 of International Application Number PCT/FR02/04498 filed on Dec. 20, 2002.

A subject matter of the present invention is the use of charged random polymers as thickening agent for aqueous compositions comprising one or more surfactants organized as a phase of giant micelles, and compositions comprising such organized phases thickened by said polymers.

The field of the present invention is directed at surface-active aqueous formulations which form giant micelles.

In numerous fields employing surface-active formulations, very particular attention is paid to the viscosity of the formulation. This is because it is desired to be able to have available formulations exhibiting relatively high viscosities, whether for reasons of a purely technical nature, such as, for example, the maintenance of particles in suspension, or alternatively for reasons directed at the user, such as, for example, the ease or the comfort of distribution and of use of the formulation or a particular sensory feel, indeed even for all these reasons.

The difficulty lies in the fact that aqueous surface-active formulations exhibit viscosities which are regarded as too low for a good number of applications.

Various solutions to this drawback have been introduced.

Thus, salts, such as typically sodium chloride, have been used as rheology-modifying agent. However, the amount of this type of compound cannot be too high or there will be a risk of having harmful effects on the formulation.

The use of polymers, such as modified or unmodified polysaccharide derivatives, or such as synthetic polymers of the type of crosslinked polyacrylates, for example, has also been developed. The difficulties encountered during the use of these additives are due in particular to the fact that they have to be employed, in some cases, in large amounts, that they can be relatively complex for making use of and/or that their operating range is limited as their stability depends on the pH of the formulation and on the concentration of salt in the formulation.

Finally, giant micelles represent a category of organized phase of surfactants which is desired as, among other advantages, they confer specific Theological properties on the formulation. In particular, they develop higher viscosities than solutions of surfactants not possessing them, when it is desired to limit the concentrations of surfactants and/or of salt.

The problem is that the increase in viscosity brought about by virtue of the presence of the giant micelles may not be regarded as sufficient.

There is therefore still a search for thickening additives to be added to aqueous surface-active compositions, which additives would in particular be stable under various conditions of pH and of concentration of salts and which would be effective at relatively low concentrations.

Furthermore, the targeted additives would make it possible to obtain formulations exhibiting additional specific-characteristics. Thus, it is desirable to be able to have available additives which do not make it impossible to obtain transparent formulations or which give the formulation additional functional properties, such as a conditioning effect, for example, characteristics desired more especially in the field of formulations intended for the treatment of the skin and/or hair. Furthermore, in other fields, such as in particular that of the exploitation of oil or gas deposits, it is desirable to be able to employ additives which contribute improved thermal stability to the formulation in which they participate.

These aims and others are achieved by the present invention, a first subject matter of which is therefore the use, as thickening agent for an aqueous composition comprising at least 5% by weight of one or more surfactant(s) organized as a phase comprising giant micelles, the mean length of which represents at least 4 times the mean diameter, of at least one ionically charged random amphiphilic polymer which is soluble in the aqueous composition; said amphiphilic polymer being used with a content such that the viscosity of the aqueous composition comprising the amphiphilic polymer is at least three times greater than that of the composition devoid of amphiphilic polymer and than that of an aqueous solution comprising the amphiphilic polymer alone.

A subject-matter of the invention is likewise an aqueous composition comprising at least 5% by weight of one or more surfactant(s) organized as a phase comprising giant micelles, the mean length of which represents at least 4 times the mean diameter, and comprising at least one ionically charged random amphiphilic polymer which is soluble in the aqueous composition; said amphiphilic polymer being used with a content such that the viscosity of the aqueous composition comprising the amphiphilic polymer is at least three times greater than that of the composition devoid of amphiphilic polymer and than that of an aqueous solution comprising the amphiphilic polymer alone.

This is because it has been found, entirely unexpectedly, that aqueous formulations comprising an organized phase of surfactant(s), of the type of the giant micelles, could be effectively thickened when a charged random amphiphilic polymer was added thereto. This is all the more surprising as said polymer is not in itself a thickening agent for aqueous solutions. Thus, in contrast to conventional systems comprising polymers having intrinsic thickening agent properties, the polymers employed in the context of the present invention are not thickeners as such for the aqueous phase but nevertheless significantly increase the Theological properties (viscosity, viscoelasticity) initially introduced by the giant micelles.

Furthermore, it has been observed that said random polymer, in addition to its role of thickening agent for formulations comprising giant micelles, has, under the same conditions, a role of dispersing agent for particles.

According to another advantageous characteristic of the invention, it has also been noticed that said polymer, still under the same conditions, has an additional role of emulsifying agent for a phase which is immiscible with the aqueous formulation and/or of stabilizing agent for such a phase.

Finally, it has been found that said random polymer, under the same conditions, has an additional role of helping in the deposition of particles or emulsions on a surface.

However, other advantages and characteristics of the invention will become more clearly apparent on reading the description and examples which will follow.

The invention thus relates to the thickening of aqueous compositions comprising at least one surfactant with a content of at least 5% by weight with respect to the weight of the composition, preferably a content of between 5 and 15% by weight.

It is specified that the compositions are more particularly formulations which can used in various fields and in particular in the field of the treatment of the skin and/or hair or in the field of the exploitation of oil or gas deposits.

These compositions exhibit an organized phase of surfactant(s) which is of the "giant micelle" type.

This type of organized phase intrinsically develops a specific viscosity but one which always remains insufficient.

Within the meaning of the invention, the term "giant micelles" denotes objects dispersed in the aqueous composition and for which the mean length represents at least four times the mean diameter of these vesicles. These objects are well known to a person skilled in the art and they are referred to in publications under the names, inter alia, of "worm-like micelles" or "living polymers".

These micelles can in particular be observed, for example, using an electron microscope.

More particularly, the mean length of the giant micelles is usually greater than or equal to 10 times that of the diameter. It is preferably greater than or equal to 100 times that of the diameter.

The surfactant or surfactants are chosen from those which give organized phases of giant micelle type when they are in aqueous solution.

According to a specific embodiment of the invention, the aqueous composition comprises at least one surfactant which, at a concentration in water of greater than or equal to 5% by weight, gives an organized phase of giant micelle type under the conditions of use of the composition (that is to say, under the conditions of concentrations, of pH, of ionic strength, of temperature).

The choice of the surfactant does not represent per se a particular difficulty for a person skilled in the art.

Nevertheless, there are several scenarios.

According to a first alternative form, the surfactant (or main surfactant) is chosen from the entities which, alone, are capable of forming a giant micelle phase under the conditions of concentration, temperature, pH and ionic strength of the composition.

To define the suitable surfactant, a person skilled in the art can proceed by plotting out the phase diagram in order to determine in what concentration range the desired phase exists, if such is the case, and subsequently observe whether this range is compatible with the conditions of temperature, pH, ionic strength and temperature of the composition.

According to this first alternative form, it may be advantageous to combine, with the main surfactant chosen, either at least one salt or at least one cosurfactant, indeed even the combination of these two types of compounds. The advantage of employing additives of this type is that they represent a means for reducing the content of main surfactant, in order to obtain the giant micelle phase, or alternatively, in other words, for increasing the level of viscosity of the composition at the same concentration of main surfactant.

As regards the choice of the possible cosurfactant, it is preferably chosen according to the nature of the abovementioned main surfactant and can in particular be a surfactant with a net charge opposite that of the main surfactant or alternatively a surfactant of amphoteric type. It can also be chosen from nonionic surfactants.

According to a second alternative form of the invention, the main surfactant is chosen from those which make possible access to a phase of giant micelles in the presence of at least one salt and/or at least one cosurfactant.

A person skilled in the art, according to this second alternative form, will proceed in a similar way to the preceding alternative form, in order to determine the surfactant/salt and/or cosurfactant combination which will make it possible, under the conditions of concentration, temperature, pH and ionic strength of the composition, to access the giant micelle phase.

Mention may in particular be made, as examples of suitable surfactants which can be used as main surfactant, of nonionic surfactants derived from linear or branched aliphatic alcohols comprising 6 to 24 carbon atoms and comprising oxyethylene and optionally oxypropylene units in a content such that the surfactant exhibits an HLB value of at least 10. Purely by way of illustration, the number of oxyethylene and optionally oxypropylene units is between 2 and 10.

Arrangements of surfactants as a phase comprising giant micelles which are particularly advantageous are arrangements such that the aqueous composition exhibits viscoelastic properties. Such compositions and/or arrangements are disclosed in particular in the international patent application published under the number WO 98/56497. The addition of the charged amphiphilic polymer to these compositions increases the viscosity, the composition furthermore retaining viscoelastic properties.

Amphoteric or zwitterionic surfactants are advantageous surfactants in obtaining an arrangement as a phase comprising giant micelles. Examples of zwitterionic surfactants which can be used comprise compounds of formula $R^1R^2R^3N^+$—$R^4COO^-$ where $R^1$ is a hydrophobic alkyl, alkylarylalkyl, alkoxyalkyl, alkylaminoalkyl or allylamidoalkyl group where the alkyl part is from $C_{12}$ to $C_{24}$, $R^2$ and $R^3$, which are identical or different, are $C_1$ to $C_{30}$ aliphatic chains (that is to say, the atom of which is bonded to the nitrogen atom does not form part of an aromatic group), for example a methyl, ethyl, benzyl, hydroxyethyl, hydroxyethyl, acetate or propionate group, and $R^4$ is a divalent hydrocarbonaceous group, such as a methylene or ethylene group. Examples of amphoteric surfactants which can be used comprise compounds of formula $R^1R^2NH^+$—$R^4COO^-$ where $R^1$, $R^2$ and $R^4$ are as mentioned above.

It may also be possible to employ, as main surfactant, at least one surfactant chosen from the following anionic entities:

alkyl ester sulfonates, for example of formula R—CH($SO_3M$)-COOR', where R represents a $C_8$-$C_{20}$, preferably $C_{10}$-$C_{16}$ alkyl radical, R' is a $C_1$-$C_6$, preferably $C_1$-$C_3$, alkyl radical, and M an alkali metal cation (sodium, potassium or lithium), a substituted or unsubstituted ammonium (methyl-, dimethyl-, trimethyl- or tetramethylammonium, dimethylpiperidinium, and the like) cation or a cation derived from an alkanolamine (monethanolamine, diethanolamine, triethanolamine, and the like). Mention may very particularly be made of the methyl ester sulfonates for which the R radical is a $C_{14}$-$C_{16}$ radical; alkylbenzene-sulfonates, more particularly $C_9$-$C_{20}$ alkylbenzene-sulfonates, primary or secondary alkylsulfonates, in particular $C_8$-$C_{22}$ alkylsulfonates, alkylglycerol sulfonates, sulfonated polycarboxylic acids, such as, for example, those disclosed in GB 1082179, or paraffin sulfonates;

alkyl sulfates, for example of formula $ROSO_3M$, where R represents a $C_{10}$-$C_{24}$, preferably $C_{12}$-$C_{20}$, alkyl or hydroxyalkyl radical; M representing a hydrogen atom or a cation with the same definition as above, and their polyalkoxylated derivatives (ethoxylated (EO) derivatives, propoxylated (PO) derivatives, or their combinations), such as, for example, sodium dodecyl sulfate;

alkyl ether sulfates, for example of formula $RO(CH_2CH_2O)_nSO_3M$, where R represents a $C_{10}$-$C_{24}$, preferably $C_{12}$-$C_{20}$, alkyl or hydroxyalkyl radical; M representing a hydrogen atom or a cation with the same definition as above, n generally varying from 1 to 4, and their polyalkoxylated derivatives (ethoxylated (EO) derivatives, propoxylated (PO) derivatives, or their combinations), such as, for example, the lauryl ether sulfate with n=2;

alkylamides sulfates, for example of formula RCONHR'OSO$_3$M, where R represents a C$_2$-C$_{22}$, preferably C$_6$-C$_{20}$, alkyl radical, R' represents a C$_2$-C$_3$ alkyl radical, M representing a hydrogen atom or a cation with the same definition as above, and their polyalkoxylated derivatives (ethoxylated (EO) derivatives, propoxylated (PO) derivatives, or their combinations);

salts of saturated or unsaturated fatty acids, for example such as those of C$_8$-C$_{24}$, preferably C$_{14}$-C$_{20}$, fatty acids, N-acyl-N-alkyltaurates, alkyl isethionates, alkylsuccinamates and alkylsulfosuccinates, the monoesters or diesters of sulfosuccinates, N-acylsarcosinates or polyethoxycarboxylates; and alkyl and/or alkyl ether and/or alkylaryl ether phosphate esters.

As regards the salts capable of being used, mention may be made of the salts of inorganic acids, such as the salts of hydrochloric acid (sodium or potassium). Suitable salts also include the salts of organic acids, the counterion of which is chosen from those capable of reducing the value of the HLB (hydrophilic/lipophilic balance) of the main surfactant. Mention may be made, as specific example of salts of this type, of cetyltrimethylammonium salicylate chloride.

If a salt is present, and whatever the alternative form chosen, its content usually represents a concentration of between 0.1 and 5% by weight of the composition.

As regards the possible cosurfactant, the latter can be chosen from the following surfactants, used alone or combined:

alkyl amphoacetates and alkyl amphodiacetates corresponding more generally to the formula: RCO—NH$_a$(CH$_2$COONa)$_{1-a}$—CH$_2$CH$_2$—N(CH$_2$COONa)—CH$_2$CH$_2$—OH; in which formula R represents an alkyl or alkenyl radical comprising 10 to 24 carbon atoms, a is equal to 0 or 1 and R represents more particularly coco and lauryl chains (for example, the Miranol C2M and Miranol Ultra C32 compounds from Rhodia Chimie);

alkyl amphopropionates or alkyl amphodipropionates, more particularly of formula: RCO—NH$_a$(CH$_2$CH$_2$COONa)$_{1-a}$—CH$_2$CH$_2$—N(CH$_2$CH$_2$COONa)—CH$_2$CH$_2$—OH; the Miranol C2M SF products from Rhodia Chimie are examples thereof;

alkyl amphohydroxypropyl sultaines, such as, for example, the Miranol CS compounds from Rhodia Chimie.

Mention may in particular be made, among zwitterionic surfactants which can used as cosurfactant, of, alone or as mixtures, betaines, for example of formula R(R')$_3$N$^+$—COO$^-$, in which formula the R radical represents an alkyl or alkenyl radical comprising 10 to 24 carbon atoms and R', which is identical or different, represent an alkyl or alkenyl radical having from 1 to 4 carbon atoms. Mention may particularly be made, by way of example, of lauryl betaine (Mirataine BB from Rhodia Chimie);

sulfobetaines, for example of following formula: R(R')$_3$N$^+$—SO$_3$—, in which formula the R and R' radicals have the same meaning as above;

amidoalkylbetaines, in particular of following formula: RCO—NHR'—N$^+$(R')$_3$—COO$^-$, in which formula the R and R' radicals have the same meaning as above. Cocamidopropylbetaine (Mirataine BDJ from Rhodia Chimie) is an example of this type of compound;

sulfoamidoalkyl betaines, for example of following formula: RCO—NHR'—N$^+$(R')$_3$—SO$_3$—, R and R' having the same meaning as previously.

In the case where a nonionic surfactant is employed as cosurfactant, mention may be made, inter alia, of
optionally alkoxylated fatty alcohols,
alkoxylated mono-, di- and triglycerides,
alkoxylated fatty acids,
alkoxylated sorbitan esters,
alkoxylated fatty amines,
alkoxylated alkylphenols,
alkylpolyglucosides, alone or as a mixture.

The optionally alkoxylated fatty alcohols generally comprise from 4 to 24 carbon atoms, their alkoxy units being excluded from these numbers.

The alkoxylated mono-, di- and triglycerides can be mono-, di- and triglycerides of vegetable or animal origin.

The optionally alkoxylated sorbitan esters are cyclic esters of sorbitol with a fatty acid comprising 10 to 20 carbon atoms such as lauric acid, stearic acid or oleic acid.

The alkoxylated fatty amines generally have from 10 to 22 carbon atoms, the alkoxyl units being excluded from these numbers.

The alkoxylated alkylphenols generally have one or two linear or branched alkyl groups having 4 to 12 carbon atoms. Mention may in particular be made, by way of example, of the octyl, nonyl or dodecyl groups.

The alkylpolyglucosides are more specifically nonionic oligomeric surfactants which exist in the form of acetals of fatty alcohols (preferably C8-C16 fatty alcohols) and sugars (glucose). They are obtained in particular by chemical reaction starting from starch, from fats. Such surfactants are, for example, sold by Henkel under the Plantaren® names.

In the case where a cosurfactant is present, whatever the alternative form selected, its content is such that the cosurfactant/main surfactant ratio by weight is less than 50/50, preferably between 0.1/99.9 and 40/60.

The random polymer participating in the aqueous composition is first of all chosen from those which are charged and soluble in the aqueous composition. It is specified that it is preferably not a crosslinked or branched polymer. It is preferably a linear polymer.

Said amphiphilic polymer employed in the context of the present invention can be either a polymer of polyanion type, that is to say a polymer which, as regards the charged monomers, carries only negative ionic charges, or a polymer of polycation type, that is to say carrying only positive ionic charges; or alternatively a polymer of polyampholyte type, that is to say carrying both positive and negative ionic charges.

It should be noted that the existence of ionic charge(s) is observed under the conditions of temperature, of pH and of ionic strength of the aqueous composition.

Furthermore, the solubility of the amphiphilic polymer depends on the pH, on the respective concentrations of the various constituent components and on the temperature of use and of preparation of said aqueous composition.

Moreover, a polymer will be said to be "soluble" within the meaning of the invention if the aqueous composition comprising said polymer, after 2 hours, does not exhibit macroscopic phase separation at approximately 20° C.

Furthermore, the polymer which can be used in the invention may in fact exist in the form of an oligomer, that is to say of an entity having a mean degree of polymerization of between 3 and 10, or of a polymer, that is to say of an entity having a mean degree of polymerization of greater than 10. In that which follows, only the term of polymer will be used, it being known that it covers the two possibilities which have just been set out.

Thus, the polymer, under the pH conditions of the aqueous composition, exhibits a coefficient f of at least 0.05, more particularly of between 0.05 and 2. It should be remembered that this coefficient f represents the fraction of total charge of the amphiphilic polymer and that it corresponds to the sum of the number of moles of theoretical charges of monomers carrying a charge (anionic or cationic) in the polymer, divided by the sum of the total theoretical number of moles of monomers in said amphiphilic polymer.

Moreover, according to a specific embodiment of the invention, the amphiphilic polymer exhibits a coefficient $\Delta f$ of between −0.5 and 0.5.

It should be remembered that the coefficient $\Delta f$ corresponds to the difference between the theoretical number of moles of cationic charges and the theoretical number of moles of anionic charges of the polymer, the whole being divided by the sum of the total theoretical number of moles of monomers of the polymer.

More particularly, according to a first embodiment of the invention, the amphiphilic polymer is chosen from those comprising a neutral net charge. In other words, the polymers participating in this embodiment exhibit a coefficient $\Delta f$ of between −0.1 and 0.1 (the number of theoretical moles of cationic charges in the monomer is similar to that of the number of theoretical moles of anionic charges).

According to a second embodiment of the invention, the amphiphilic polymer has a net charge opposite that of the main surfactant.

A first alternative form of this second embodiment consists in employing a polymer having a $\Delta f$ value of between 0.1 exclusive and 0.5. According to this first alternative form, the polymer has a theoretical number of moles of cationic charges in the amphiphilic polymer which is greater than that of the anionic charges. In this case, this amphiphilic polymer is preferably employed when the surfactant or surfactants which bring about the giant micelle phase are of anionic type.

Furthermore, and in a symmetrical fashion, the second alternative form of this second embodiment consists in employing a polymer having a $\Delta f$ value of between −0.5 and −0.1 exclusive. According to this alternative form, the polymer has a theoretical number of moles of anionic charges in the amphiphilic polymer which is greater than that of the cationic charges. In this case, this amphiphilic polymer is preferably employed when the surfactant or surfactants which bring about the giant micelle phase are of cationic type.

The amphiphilic polymer employed as thickening agent furthermore comprises hydrophobic units. These units, comprising at least 6 carbon atoms, are preferably more particularly of the following type: linear or branched alkyl or aryl optionally carrying one or more linear or nonlinear alkyl radicals. It is specified that the aryl radical can be attached directly to the backbone of the polymer or else can be attached thereto via an alkyl radical.

Preferably, the identical or different hydrophobic units are branched alkyl radicals comprising 6 to 24 carbon atoms, preferably 6 to 10 carbon atoms, or aryl radicals of benzyl type optionally carrying one or more linear or nonlinear alkyl radicals.

The monomers from which the hydrophobic units are obtained can be nonionic but can also carry an ionic charge (anionic or cationic).

Mention may be made, as examples of suitable nonionic monomers from which the hydrophobic units of the random polymer can be obtained, of, alone or as mixtures:

esters of linear, branched, cyclic or aromatic mono- or polycarboxylic acids comprising at least one ethylenic unsaturation;

$\alpha,\beta$-ethylenically unsaturated nitriles, vinyl esters or vinylaromatic monomers, linear or branched, aromatic or nonaromatic, hydrocarbonaceous monomers comprising at least one ethylenic unsaturation.

Mention may be made, as preferred examples of such monomers, of the esters of (meth)acrylic acid with an alcohol comprising at least 6 to 24, preferably 6 to 10, carbon atoms, such as 2-ethylhexyl acrylate or methacrylate; styrene, $\alpha$-methylstyrene or vinyltoluene, alone or as mixtures.

As regards the cationic hydrophobic monomers, mention may be made, inter alia, of the following monomers, comprising at least one alkyl or aromatic radical having at least 6 carbon atoms, and of the type:

aminoalkyl (meth)acrylates, aminoalkyl(meth)-acrylamides, or their salts;

monomers comprising at least one secondary, tertiary or quaternary amine functional group or a heterocyclic group comprising a nitrogen atom, or their salts;

diallyldialkylammonium salts;

alone or as mixtures, in which the alkyl group comprises 6 to 24, preferably 6 to 10, carbon atoms.

If they are provided in the form of salts, the latter are preferably chosen such that the counterion is a halide, such as, for example, a chloride, or a sulfate, a hydrosulfate, an alkyl sulfate, a phosphate, a citrate, a formate or an acetate.

Furthermore, the ammonium ion comprises at least one alkyl radical or at least one aryl radical optionally carrying one or more alkyl radicals having at least 6 carbon atoms.

As regards the anionic monomers, the latter are more particularly chosen from those comprising at least one alkyl radical or at least one aromatic radical having at least 6 carbon atoms and carrying at least one carboxylic, sulfonic, sulfuric, phosphonic, phosphoric or sulfosuccinic functional group, their salts or their precursors.

More particularly, the anionic units of the copolymer are obtained from at least one monomer chosen from linear, branched, cyclic or aromatic carboxylic acids, linear, branched, cyclic or aromatic vinylcarboxylic acids, alone or as mixtures, their sulfonic or phosphonic derivatives.

Preferably, the hydrophobic unit(s) of the random polymer are obtained from nonionic hydrophobic monomer(s).

Preferably, the theoretical number of moles of hydrophobic monomers present in the composition of the amphiphilic polymer is at least 5% with respect to the total theoretical number of moles of monomers of the polymer.

In the case where the hydrophobic units are alkyl radicals, the theoretical number of moles of hydrophobic monomers present in the composition of the amphiphilic polymer is between 10 and 50%, preferably between 25 and 40%, by weight with respect to the total theoretical number of moles of monomers of the polymer.

In the case where the hydrophobic units are aryl radicals, the theoretical number of moles of hydrophobic monomers present in the composition of the amphiphilic polymer is between 5 and 15% by weight with respect to the total theoretical number of moles of monomers of the polymer.

It is specified that the true molar contents in the polymer, determined by NMR, for example, are in agreement to within about ±20% with the theoretical molar contents which have just been mentioned.

Furthermore, the amphiphilic polymer comprises hydrophilic units which can be either nonionic or anionic or cationic or amphoteric.

The monomers from which the hydrophilic units are obtained are more particularly chosen from those which, once homopolymerized with a degree of polymerization of between 40 and 100, give a polymer which is soluble under the conditions of temperature (15-35° C.) and of pH of the composition.

As regards the nonionic hydrophilic units which may be present in the amphiphilic polymer, mention may in particular be made of those obtained from the following monomers:
- amides of linear, branched, cyclic or aromatic mono- or polycarboxylic acids comprising at least one ethylenic unsaturation, or derivatives;
- vinyl esters which make it possible to obtain poly(vinyl) alcohol blocks after hydrolysis, alone or as mixtures.

As regards the nonionic hydrophilic monomers, mention may very particularly be made of (meth)acrylamide, N-methylol(meth)acrylamide, 2-hydroxyethyl(meth)acrylate, or the vinyl esters which make it possible to obtain poly(vinyl alcohol) blocks after hydrolysis, such as vinyl acetate, vinyl Versatate® or vinylpropionate.

As relates more specifically to the monomers from which cationic hydrophilic units can be introduced into the amphiphilic polymer, mention may be made, inter alia, of:
- aminoalkyl(meth)acrylates or aminoalkyl(meth)acrylamides;
- monomers comprising at least one secondary, tertiary or quaternary amine functional group or a heterocyclic group comprising a nitrogen atom, vinylamine or ethylenimine;
- diallyldialkylammonium salts;

alone or as mixtures, and their salts, in which the alkyl groups comprise less than 4 carbon atoms, preferably not more than 2.

If they are provided in the form of salts, the latter are preferably chosen so that their counterion is a halide, such as, for example, a chloride, or a sulfate, a hydrosulfate, an alkyl sulfate (for example comprising 1 to 6 carbon atoms), a phosphate, a citrate, a formate or an acetate.

Examples of suitable cationic monomers include the following monomers:
- dimethylaminoethyl(meth)acrylate, dimethylaminopropyl (meth)acrylate, di(tert-butyl)aminoethyl(meth)acrylate, dimethylaminomethyl(meth)acrylamide or dimethylaminopropyl(meth)acrylamide;
- ethylenimine, vinylamine, 2-vinylpyridine or 4-vinylpyridine;
- trimethylammonioethyl(meth)acrylate chloride, trimethylammonioethyl acrylate methyl sulfate, benzyldimethylammonioethyl(meth)acrylate chloride, 4-benzoylbenzyl-dimethylammonioethyl acrylate chloride, trimethylammonioethyl(meth)acrylamide or vinylbenzyltrimethylammonium chloride;
- diallyldimethylammonium chloride;

alone or as mixtures, or their corresponding salts.

As regards the anionic hydrophilic units, the latter can be obtained from the following monomers, and their corresponding salts, their precursors or their phosphonic or sulfonic derivatives:
- linear, branched, cyclic or aromatic mono- or polycarboxylic acids or the N-substituted derivatives of such acids;
- monoesters of polycarboxylic acids, comprising at least one ethylenic unsaturation;
- linear, branched, cyclic or aromatic vinylcarboxylic acids;
- amino acids comprising one or more ethylenic unsaturations;

alone or a mixtures.

Use may advantageously be made of the following monomers, without intending to be limited thereto:
- acrylic acid, methacrylic acid, fumaric acid, itaconic acid, citraconic acid, maleic acid, acrylamidoglycolic acid, 2-propene-1-sulfonic acid, methallylsulfonic acid, styrenesulfonic acid, α-acrylamidomethylpropanesulfonic acid, 2-sulfoethylene methacrylate, sulfopropylacrylic acid, bis(sulfopropyl)acrylic acid, bis(sulfopropyl) methacrylic acid, sulfatoethylmethacrylic acid, the phosphate monoester of hydroxyethylmethacrylic acid, and the salts of alkali metals, such as sodium or potassium, or of ammonium;
- vinylsulfonic acid, vinylbenzenesulfonic acid, vinylphosphonic acid, vinylidenephosphoric acid, vinylbenzoic acid, and the salts of alkali metals, such as sodium or potassium, or of ammonium;
- N-(methacryloyl)alanine or N-(acryloyl)hydroxy-glycine;

alone or as mixtures.

As relates to the amphoteric monomers, mention may be made, by way of illustration, of monomers of the type of the sulfobetaines, such as, in particular, (meth)acrylate of alkyl dialkylammonium alkylsulfonate, of the type of the (meth)acrylate of ethyl dimethylammonium propylsulfonate; (meth)acrylamide of alkyldialkylammonium sulfoalkyl, of the type of the (meth)acrylamide of propyl dimethylammonium sulfopropyl; vinyl pyridinium dialkylammonium sulfoalkyl, of the type of the vinylpyridinium dimethylammonium sulfopropyl, alone or as mixtures or in the form of macromonomers.

It should be noted that it would not be departing from the scope of the present invention to employ monomers which are precursors of those which have just been mentioned. In other words, these monomers exhibit units which, once incorporated in the polymer chain, can be converted, in particular by chemical treatment, such as hydrolysis, to restore the abovementioned anionic entities. For example, the completely or partially esterified monomers of the abovementioned monomers can be employed in order, subsequently, to be completely or partially hydrolyzed.

The number-average molar mass of the polymer is usually greater than or equal to 1000 g/mol. Furthermore, the number-average molar mass is preferably between 5000 and 100000 g/mol. It should be noted that the molar masses are absolute masses determined by steric exclusion chromatography coupled to a MALLS (multi-angle laser light scattering) analysis.

The polymer employed as thickening agent can be obtained according to various synthetic methods, conventional polymerizations by the radical route being particularly advantageous.

The polymerization preferably takes place in the aqueous, phase.

It usually consists in introducing the various monomers into an aqueous solution.

Moreover, it may be appropriate to add a polymerization initiator to the reaction mixture, even if this does not represent a necessary condition. This is because some monomers, such as styrene, can constitute as such a source of free radicals if the reaction temperature is sufficiently high, generally greater than 100° C.

Mention may be made, among conventional radical polymerization initiators, of, for example, hydrogen peroxides (tertiary-butyl hydroperoxide, cumene hydroperoxide, t-butyl peroxyacetate, t-butyl peraxybenzoate, t-butyl peroxyoctoate, t-butyl peroxyneodecanoate, t-butyl peroxyisobutyrate, lauroyl peroxide, t-amyl peroxypivalate, t-butyl peroxypivalate, dicumyl peroxide, benzoyl peroxide, potassium persulfate or ammonium persulfate); azo compounds (2,2'-azobis(isobutyronitrile), 2,2'-azobis(2-butanenitrile), 4,4'-azobis(4-pentanoic acid), 1,1'-azobis(cyclohexanecarbonitrile), 2-(t-butylazo)-2-cyanopropane, 2,2'-azobis[2-methyl-N-(1,1)-bis(hydroxymethyl)-2-hydroxyethyl]propionamide, 2,2'-azobis(2-methyl-N-hydroxyethyl]propionamide, 2,2'-azobis(N,N'-dimethyleneisobutyramidine)dichloride, 2,2'-azobis(2-amidinopropane)dichloride, 2,2'-azobis(N,N'-dimethyleneisobutyramide), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl]propionamide), 2,2'-azobis[2-methyl-N-(2-hydroxyethyl)propionamide] or 2,2'-azobis(isobutyramide)dihydrate); redox systems comprising combinations such as mixtures of hydrogen peroxide, alkyl peroxide, peresters, percarbonates and the like and of any of iron salts, of titanous salts, zinc formaldehydesulfoxylate or sodium formaldehyde-sulfoxylate, and reducing sugars; alkali metal or ammonium persulfates, perborates or perchlorates, in combination with an alkali metal bisulfite, such as sodium metabisulfite, and reducing sugars; alkali metal persulfates in combination with an arylphosphinic acid, such as benzenephosphonic acid and other similar compounds, and reducing sugars.

The amount of initiator to be used is determined so that the amount of radicals produced is at most 50 mol %, preferably at most 20 mol %, with respect to the amount of monomers present.

The temperature can vary between ambient temperature and 150° C. depending on the nature of the monomers used.

As indicated previously, the amphiphilic polymer is used with a content such that the viscosity of the aqueous composition comprising the amphiphilic polymer is at least three times greater than that of the composition devoid of amphiphilic polymer and than that of an aqueous solution comprising the amphiphilic polymer alone, under the same conditions of temperature, pH, ionic strength and concentration (in other words, the concentrations of the various compounds are the same as in the composition). Advantageously, the viscosity of the aqueous composition comprising the amphiphilic polymer is at least five times greater, and preferably at least ten times greater, than that of the composition devoid of amphiphilic polymer and than that of an aqueous solution comprising the amphiphilic polymer alone.

The viscosity is measured using a viscometer of Carrimed type with cone/plate geometry; the measurement is made at 25° C. with a shear gradient of 1 s$^{-1}$.

By way of illustration, the amount of amphiphilic polymer participating in the aqueous composition represents 0.5 to 5% by weight of the aqueous composition, preferably between 0.1 and 2% by weight of the aqueous composition.

The surface-active aqueous composition comprising the amphiphilic polymer can be employed in numerous fields of application but the aqueous composition is preferably a cosmetic composition more particularly intended to be rinsed out.

Another subject matter of the present invention is composed of an aqueous composition comprising at least 5% by weight of one or more surfactant(s) organized as a phase comprising giant micelles, the mean length of which represents at least 4 times the mean diameter, and comprising at least one random amphiphilic polymer chosen from those which, at the pH of the composition, are soluble in the aqueous composition; said polymer being used with a content such that the viscosity of the aqueous composition comprising the polymer is at least three times greater than that of the composition devoid of polymer and than that of an aqueous solution comprising the polymer alone. More particularly, the viscosity of the aqueous composition comprising the amphiphilic polymer is at least five times greater, and preferably at least ten times greater, than that of the composition devoid of amphiphilic polymer and than that of an aqueous solution comprising the amphiphilic polymer alone.

More particularly, the amphiphilic polymer exhibits a coefficient f of at least 0.05, more particularly of between 0.05 and 2, and a coefficient $\Delta f$ of between $-0.5$ and $0.5$.

Everything indicated above with respect to the amphiphilic polymer, in particular the units constituting it, their proportions and the synthetic routes, remains valid and will not be taken up again.

According to one embodiment of the invention, the aqueous composition comprises a content of amphiphilic polymer of between 0.05 and 5% by weight of the aqueous composition, preferably between 0.1 and 2% by weight of the aqueous composition. For its part, the content of surfactant is generally between 5% and 20%, for example between 5% and 10% or between 10% and 20%.

Furthermore, the aqueous composition is advantageously a cosmetic composition intended to be rinsed out, such as a shampoo. In such compositions, the content of surfactant is preferably between 10 and 20%. It is typically 12% but can be greater than or less than this value.

According to another possibility, the aqueous composition can be used in the field of the exploitation of oil or gas deposits. It can, for example, be a drilling fluid or a frac fluid.

Concrete but nonlimiting examples of the invention will now be presented.

EXAMPLES

1) Preparation of the Random Polymer

Structure and Composition of the Amphiphilic Polymer P1

The polymer is a random copolymer comprising the following monomer units:
Ethylhexyl acrylate (EHA),
Acrylic acid (AA),
Methacrylamidopropyltrimethylammonium sulfate (MES).

The mean molar ratio of these various units in the polymer is:
24% EHA, 53% AA, 23% MES.

Synthesis of the Polymer P1:

The theoretical concentration of polymer is 20% in an ethanol/water 2/1 mixture.

Synthesis is carried out according to the following batch process:

The following are added to a 1 liter reactor:

| | |
|---|---|
| Water: | 195.5 g |
| Ethanol: | 426.7 g |
| Acrylic acid: | 40.5 g |
| Methylacrylamidopropyltrimethylammonium sulfate (80% solution): | 89.3 g |
| Ethylhexyl acrylate: | 48.0 g |

At $t_0$, the mixture is heated to 75° C. under a stream of nitrogen.

At $t_0+1$, 0.32 g of azobisisobutyronitrile initiator (AIBN; Vazo 64) in 5 g of ethanol is added at 75° C.

At $t_0+3$, 0.16 g of AIBN initiator (Vazo 64) in 5 g of ethanol is again added. The temperature is increased to 80° C.

At $t_0+5$, gradual distillation of the ethanol is begun at 83° C. while adding water.

Distillation is carried out at 95° C. until there is no more distillate.

The reaction is halted.

The level of residual monomers is monitored. If this level is too high, sodium persulfate can be added until an acceptable level of residual monomers is obtained.

The product is transparent. The concentration of polymer is 40%. The pH is 2.18.

2) Use of the Polymer in Formulations for Shampooing Composition of the Shampoo Formulations Comparative Formula A (Without Polymer):

This is an aqueous formulation of giant micelles in distilled water comprising the following mixture of surfactants and of monovalent salt:

| | |
|---|---|
| Sodium lauryl ether sulfate, Empicol ESB3M (Albright & Wilson) | 14% by weight |
| Cocamidopropyl betaine, Tegobetaine L7 (Goldschmidt) | 2% by weight |
| Sodium chloride (Fluka) | 1% by weight |

The formulation is obtained by simple mixing of the preceding constituents at 25° C.

Four samples at different pH values (2, 5, 7 and 10) are subsequently prepared, the pH value being adjusted by addition of concentrated sodium hydroxide solution (1M NaOH) or of concentrated hydrochloric acid (1M HCl).

In this formula, the surfactants are organized as giant micelles which are revealed by electron microscopy.

In addition, the corresponding formulation is viscoelastic and birefringent under flow (measurement made in a Rheo-Optics device).

Formulation B According to the Invention (With Polymer):

The aqueous formulation in distilled water comprises the following mixture of surfactants, of monovalent salt and of polymer P1 obtained above:

| | |
|---|---|
| Sodium lauryl ether sulfate, Empicol ESB3M (Albright & Wilson) | 14% by weight |
| Cocamidopropyl betaine, Tegobetaine L7 (Goldschmidt) | 2% by weight |
| Sodium chloride (Fluka) | 1% by weight |
| Polymer P1 | 1% by weight |

Four samples, comprising the surfactants and the salt, at different pH values (2, 5, 7 and 10) are prepared in the same way as for formulation A.

The polymer P1 is dissolved in water separately at the same pH as the formulation to which it has to be added.

The formulation is obtained by mixing this polymer solution with the first mixture.

Rheological Performance of the Two Formulations

The viscosity measurements are carried out on a Carrimed at a temperature of 25° C. on the shampoo formulations A and B prepared at different pH values.

The viscosities (in mPa·s), measured for a set shear gradient, $\gamma=10\ s^{-1}$, are listed in the following table.

| | pH | | | |
|---|---|---|---|---|
| | 2 | 5 | 7 | 10 |
| Viscosity of the shampoo A | 150 | 43 | 27 | 18 |
| Viscosity of the shampoo B | 12 000 | 4750 | 5000 | 1250 |

The addition of polymer results in an increase in viscosity, whatever the pH considered in this example.

What is claimed is:

1. A process for thickening an aqueous composition comprising at least 5% by weight of one or more surfactant(s) organized as a phase comprising giant micelles, the mean length of which represents at least 4 times the mean diameter, said process comprising the step of adding to said aqueous composition at least one charged random amphiphilic polymer which is soluble in the aqueous composition; said amphiphilic polymer being added in a content such that the viscosity of the aqueous composition comprising the amphiphilic polymer is at least three times greater than that of the composition devoid of amphiphilic polymer and than that of an aqueous solution comprising the amphiphilic polymer alone.

2. The process as claimed in claim 1, wherein the amphiphilic polymer exhibits a coefficient f of at least 0.05.

3. The process as claimed in claim 1, wherein the amphiphilic polymer has a neutral net charge.

4. The process as claimed in claim 1, wherein the amphiphilic polymer comprises a net charge opposite that of the surfactant or surfactants organized as a phase comprising giant micelles.

5. The process as claimed in claim 1, wherein the amphiphilic polymer exhibits a value of $\Delta f$ of between −0.5 and 0.5.

6. The process as claimed in claim 1, wherein the polymer comprises hydrophobic units comprising at least 6 carbon atoms which are linear or branched alkyl or aryl optionally carrying one or more linear or nonlinear alkyl radicals.

7. The process as claimed in claim 6, wherein the amphiphilic polymer presents a theoretical number of moles of hydrophobic monomers present in its composition of is at least 5% with respect to the total theoretical number of moles of monomers of the polymer.

8. The process as claimed in claim 7, wherein the hydrophobic units are alkyl radicals and in that the theoretical number of moles of hydrophobic monomers present in the composition of the amphiphilic polymer is between 10 and 50%, by weight with respect to the total theoretical number of moles of monomers of the polymer.

9. The process as claimed in claim 7, wherein the hydrophobic units are aryl radicals, the theoretical number of moles of hydrophobic monomers present in the composition of the amphiphilic polymer is between 5 and 15% by weight with respect to the total theoretical number of moles of monomers of the polymer.

10. The process as claimed in claim 1, wherein the amphiphilic polymer presents nonionic hydrophilic units obtained from the following monomers:

amides of linear, branched, cyclic or aromatic mono- or polycarboxylic acids comprising at least one ethylenic unsaturation, or derivatives; or vinyl esters which make it possible to obtain poly(vinyl) alcohol blocks after hydrolysis.

11. The process as claimed in claim 1, wherein the amphiphilic polymer presents cationic hydrophilic units obtained from the following monomers, and their corresponding salts:

aminoalkyl (meth)acrylates or aminoalkyl(meth)acrylamides;

monomers comprising at least one secondary, tertiary or quaternary amine functional group or a heterocyclic group comprising a nitrogen atom, vinylamine or ethylenimine; or diallyldialkylammonium salts.

12. The process as claimed in claim 1, wherein the amphiphilic polymer presents anionic hydrophilic units obtained from the following monomers, and their corresponding salts, their precursors or their phosphonic or sulfonic derivatives:

linear, branched, cyclic or aromatic mono- or polycarboxylic acids or the N-substituted derivatives of such acids; monoesters of polycarboxylic acids, comprising at least one ethylenic unsaturation;

linear, branched, cyclic or aromatic vinylcarboxylic acids; or amino acids comprising one or more ethylenic unsaturations.

13. The process as claimed in claim 1, wherein the content of amphiphilic polymer represents 0.05 to 5% by weight of the aqueous composition.

14. The process as claimed in claim 13, wherein the content is between 0.1 and 2% by weight of the aqueous composition.

15. The process as claimed in claim 1, wherein the aqueous composition is a cosmetic composition optionally intended to be rinsed out.

16. The process as claimed in claim 1, wherein the aqueous composition is a composition for the exploitation of oil or gas deposits.

17. An aqueous composition comprising at least 5% by weight of one or more surfactant(s) organized as a phase comprising giant micelles, the mean length of which represents at least 4 times the mean diameter, and having at least one charged random amphiphilic polymer chosen from those which, at the pH of the composition, are soluble in the aqueous composition; said polymer being used with a content such that the viscosity of the aqueous composition comprising the polymer is at least three times greater than that of the composition devoid of polymer and than that of an aqueous solution comprising the polymer alone.

18. The composition as claimed in claim 17, wherein the amphiphilic polymer exhibits:

a value of the parameter f, corresponding to the sum of the theoretical number of moles of monomers carrying a charge in the polymer, divided by the sum of the total theoretical number of moles of monomers in the polymer, of at least 0.05, and a value of $\Delta f$, corresponding to the difference between the theoretical number of moles of cationic monomers and the theoretical number of moles of anionic monomers of the polymer, divided by the sum of the total theoretical number of moles of the polymer, is between $-0.5$ and $0.5$.

19. The composition as claimed in claim 18, wherein the amphiphilic polymer comprises a neutral net charge or a charge opposite that of the surfactant or surfactants organized as a phase comprising giant micelles.

20. The composition as claimed in claim 19, wherein the theoretical number of moles of hydrophobic monomers present in the polymer is at least 5% with respect to the total theoretical number of moles of monomers present in the polymer.

21. The composition as claimed in claim 17, wherein the aqueous composition is a cosmetic composition intended to be rinsed out.

22. The composition as claimed in claim 17, wherein the aqueous composition is a composition which can be used in the exploitation of oil or gas deposits.

23. The composition as claimed in claim 17, wherein the content of amphiphilic polymer represents 0.05 to 5% by weight of the aqueous composition.

24. The composition as claimed in claim 23, wherein the content of amphiphilic polymer represents between 0.1 and 2% by weight of the aqueous composition.

25. A process comprising:

adding at least one charged random amphiphilic polymer to an aqueous composition comprising at least 5% by weight of one or more surfactants;

wherein said charged random amphiphilic polymer is added in an amount such that the viscosity of the aqueous composition is at least three times greater than that of the composition devoid of said amphiphilic polymer and the viscosity of the aqueous composition is at least three times greater than that of an aqueous solution comprising the amphiphilic polymer alone;

further wherein said charged random amphiphilic polymer is soluble in the aqueous composition and is not itself a thickening agent for aqueous solutions; and further wherein said one or more surfactants are organized as a phase comprising giant micelles having a length at least 4 times their mean diameter.

* * * * *